United States Patent [19]

White et al.

[11] Patent Number: 4,640,924
[45] Date of Patent: Feb. 3, 1987

[54] THIENOQUINOLIZINES AND THEIR USE AS α2-ADRENOCEPTOR ANTAGONISTS

[75] Inventors: Alan C. White, Englefield Green; Robin G. Shepherd, Maidenhead; Barry J. Langham, Slough, all of England

[73] Assignee: John Wyeth & Brother Limited, Maidenhead, England

[21] Appl. No.: 764,904

[22] Filed: Aug. 12, 1985

[30] Foreign Application Priority Data

Aug. 14, 1984 [GB] United Kingdom ............... 8420602

[51] Int. Cl.[4] .................. A61K 31/38; C07D 455/04
[52] U.S. Cl. ...................................... 514/291; 546/80
[58] Field of Search ......................... 546/80; 514/291

[56] References Cited

U.S. PATENT DOCUMENTS

| | | | |
|---|---|---|---|
| 4,060,619 | 11/1977 | Philipp et al. | 546/80 |
| 4,454,139 | 6/1984 | Ward et al. | 546/80 |
| 4,473,572 | 9/1984 | Ward | 546/80 |
| 4,481,200 | 11/1984 | Ward et al. | 546/80 |
| 4,526,967 | 7/1985 | Ward | 546/80 |

Primary Examiner—Henry R. Jiles
Assistant Examiner—J. Richter
Attorney, Agent, or Firm—George Tarnowski

[57] ABSTRACT

The invention concerns thienoquinolizines of general formula (I)

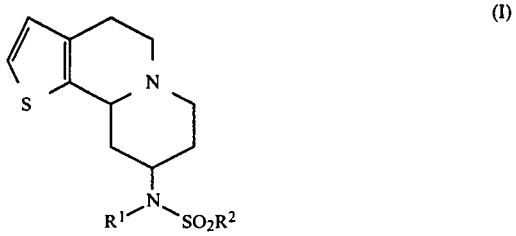

and their pharmaceutically acceptable acid addition salts. In the formula $R^1$ is hydrogen or lower alkyl and $R^2$ is lower alkyl, halo(lower)alkyl, —A—$NR^3R^4$ [where A represents a direct bond between the S and N atoms or a lower alkylene group having 1 to 3 carbon atoms in the chain between the S and N atoms and $R^3$ and $R^4$ each independently represent hydrogen, lower alkyl, aryl or aryl(lower)alkyl or together with the nitrogen atom to which they are attached represent a five or six membered heterocyclic ring], aryl or a heterocyclic radical or $R^1$ is —$A^1NR^5.SO_2R^6$ [where $A^1$ is a lower alkylene group having 1 to 3 carbon atoms in the chain between the two N atoms, $R^5$ is hydrogen or lower alkyl and $R^6$ is lower alkyl, halo(lower)alkyl or aryl] and $R^2$ is lower alkyl, halo(lower)alkyl or aryl. The compounds possess α2-adrenoceptor antagonistic activity in warm blooded animals.

5 Claims, No Drawings

THIENOQUINOLIZINES AND THEIR USE AS α₂-ADRENOCEPTOR ANTAGONISTS

The invention relates to thienoquinolizines, to processes for preparing the thienoquinolizines, to their use and to pharmaceutical compositions containing them.

The novel compounds of the present invention are thienoquinolizines of the general formula (I)

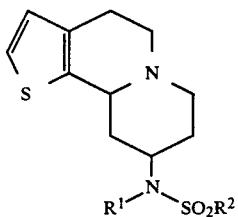

(I)

and their pharmaceutically acceptable acid addition salts, where $R^1$ is hydrogen or lower alkyl and $R^2$ is lower alkyl, halo(lower)alkyl, —A—$NR^3R^4$ [where A represents a direct bond between the S and N atoms or a lower alkylene group having 1 to 3 carbon atoms in the chain between the S and N atoms and $R^3$ and $R^4$ each independently represent hydrogen, lower alkyl, aryl or aryl(lower)alkyl or together with the nitrogen atom to which they are attached represent a five or six membered heterocyclic ring], aryl or a heterocyclic radical or $R^1$ is —$A^1NR^5.SO_2R^6$ [where $A^1$ is a lower alkylene group having 1 to 3 carbon atoms in the chain between the two N atoms, $R^5$ is hydrogen or lower alkyl and $R^6$ is lower alkyl, halo(lower)alkyl or aryl] and $R^2$ is lower alkyl halo(lower)alkyl or aryl.

The term "lower" as used herein means that the radical referred to contains 1 to 6 carbon atoms. Preferably such radicals contain 1 to 4 carbon atoms. For example, a lower alkyl group may be methyl, ethyl, propyl or butyl (e.g. i-butyl).

When A represents a lower alkylene group, the group may be branched or straight chain provided that there are 1 to 3 carbon atoms in the chain between the S and N atoms. Similarly, the lower alkylene group $A^1$ has 1 to 3 carbon atoms between the two N atoms. For example, the lower alkylene group A and $A^1$ may be methylene, ethylene, trimethylene or a branched chain group such as ethylethylene or propylene [—CH(CH₃).CH₂—].

When a radical is referred to as "aryl" that radical is preferably a phenyl or substituted phenyl group. The substituted phenyl group can be a phenyl group substituted by one or more substituents chosen from, for example, halogen (e.g. chlorine, fluorine or bromine), alkoxy (e.g. lower alkoxy such as methoxy or ethoxy), lower alkyl (e.g. methyl, ethyl, propyl or butyl), alkylenedioxy (e.g. methylenedioxy or ethylenedioxy), nitro, amino, acylamino (particularly lower acylamino), lower alkylamino, diloweralkylamino or trifluoromethyl.

A halo substituent in a halo(lower)alkyl group may be fluorine, chlorine, bromine or iodine. More than one halo atom may be present in the halo(lower)alkyl group; if more than one halo atom is present the halo atoms may be on the same carbon atom of the (lower)alkyl radical or on different carbon atoms (if the radical contains more than one carbon atom). Examples of halo(lower)alkyl groups include, for example, trifluoromethyl and chloromethyl.

When $R^2$ is a heterocyclic radical the radical can be aromatic or non-aromatic. Preferably the heterocyclic radical is a mono or bicyclic heterocyclic group, which may be substituted or unsubstituted. The heterocyclic group may, for example, contain 1 or 2 hetero ring atoms, particularly nitrogen, oxygen or sulphur. Preferably the ring or each ring of the mono or bicyclic heterocyclic group contains 5 or 6 ring atoms (including the hetero atoms). The heterocyclic group may be substituted by one or more substituents. For example, the substituents may be selected from the group consisting of halogen (e.g. chlorine, fluorine or bromine), lower alkoxy (e.g. methoxy, ethoxy, propoxy or butoxy), lower alkyl (e.g. methyl, ethyl, propyl or butyl), alkylenedioxy (e.g. methylenedioxy or ethylenedioxy), amino, loweralkylamino, diloweralkylamino, trifluoromethyl, carbamoyl, phenyl and phenyl substituted by one or more of those substituents mentioned immediately above in connection with the heterocyclic group. Examples of heterocyclic radicals include substituted and unsubstituted quinoline, furan, thiophene, imidazole, pyridine, piperidine, pyrrolidine, indolyl and 1,2,3,4-tetrahydroquinoline.

Preferably in formula(I) $R^1$ is lower alkyl (particularly methyl or ethyl) and $R^2$ is lower alkyl or optionally substituted phenyl. Other preferred compounds are those in which $R^1$ is —$A^1$—$NR^5.SO_2R^6$ (where $A^1$ is preferably ethylene, $R^5$ is preferably hydrogen and $R^6$ is preferably lower alkyl) and $R^2$ is lower alkyl.

The compounds of the invention in which $R^1$ is hydrogen or lower alkyl can be prepared by a process in which an amine of general formula (II)

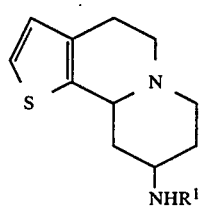

(II)

where $R^1$ is hydrogen or lower alkyl or an acid addition salt thereof, is reacted with reactive derivative of a sulphonic acid compound of general formula (III)

$R^2SO_2OH$ (III)

(where $R^2$ is as defined above) and, if required, converting a free base into a pharmaceutically acceptable acid addition salt. The reactive derivative of the sulphonic acid compound of general formula (III) can be, for example, the acid halide or anhydride. Preferably it is the halide, i.e. a compound of general formula $R^2SO_2X$ (where $R^2$ is as defined above and X is halogen, preferably chlorine). The reaction is preferably carried out under basic conditions, for example in the presence of a tertiary amine, e.g. triethylamine.

The reactive derivatives of the sulphonic acid compound of general formula (III) are known compounds or they can be prepared by methods known in the art for preparing analogous compounds.

The amine of general formula (II) in which $R^1$ is hydrogen may be prepared from the ketone (IV) by the following procedure using known methods:

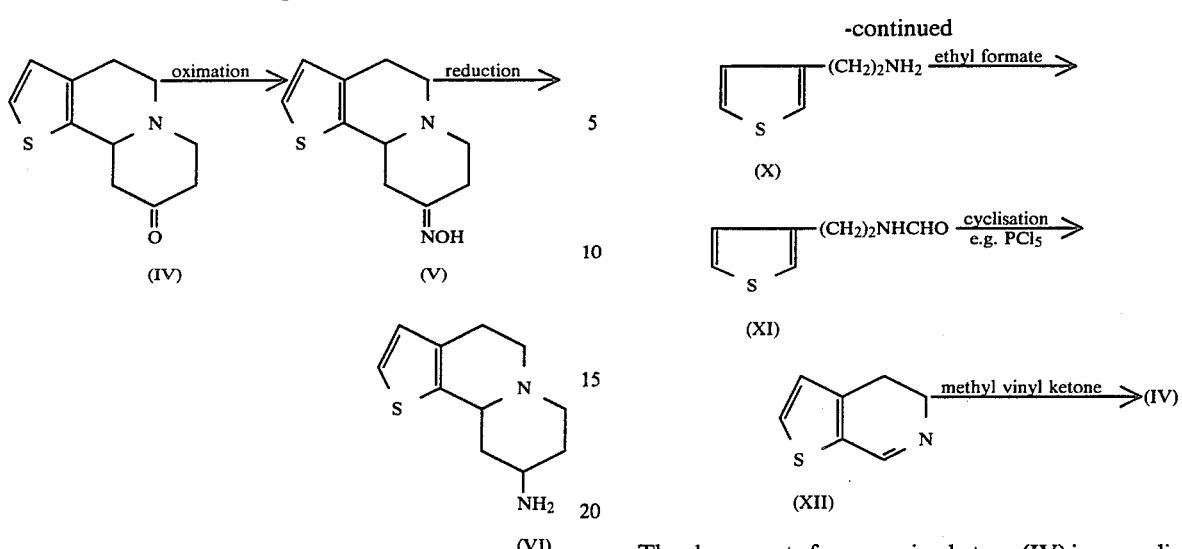

The amine of general formula (II) in which $R^1$ is lower alkyl may be prepared from the ketone (IV) by the following procedure using known methods:

The ketone of formula (IV) may be prepared by the following procedure:

The above route for preparing ketone (IV) is exemplified in Example 1(a) to (d), below.

Compounds of general formulae (II) and (IV) are novel compounds which are also provided by the present invention.

Compounds of the invention in which $R^1$ is hydrogen or lower alkyl and $R^2$ is —$NR^3R^4$ may also be prepared by reacting the amine of general formula (II) with a sulphonamide derivative of formula $$\begin{array}{c} R^3 \\ \phantom{x} \diagdown \\ \phantom{xx} N.SO_2NH_2 \\ \phantom{x} \diagup \\ R^4 \end{array}$$

(where $R^3$ and $R^4$ have the meanings given above).

Preferably both $R^3$ and $R^4$ are hydrogen, i.e. the compound is sulphamide.

Compounds of the invention in which $R^1$ is —$A^1$—$NR^5SO_2R^6$ may be prepared by reacting a reactive derivative of the sulphonic acid compound of formula (III) in which $R^2$ is the same as $R^6$ and is lower alkyl, halo(lower) alkyl or aryl, e.g. the acid halide, with a diamine of general formula (where $A^1$ and $R^5$ are as defined above). The reaction may be carried out in a similar manner to the reaction of compound (II) with the reactive derivative of the sulphonic acid derivative (III).

The starting materials of general formula (XIII) may be prepared by reductive amination of the ketone of general formula (IV). For example, the ketone (IV) may be reacted with a diamine of formula $$NH_2-A^1-NHR^5 \qquad (XIV)$$

(where $A^1$ and $R^5$ have the meanings given above) and with a hydride transfer agent. When $R^5$ in the diamine is a lower alkyl group it may be necessary to replace the hydrogen on the amino carrying the lower alkyl substituent with a protecting group, and remove the protecting group after the reductive amination.

Compounds of the invention in which $R^1$ is $-A^1-NR^5SO_2R^6$ may be prepared by other alternative methods. For example, a thienoquinolizine of general formula (XV)

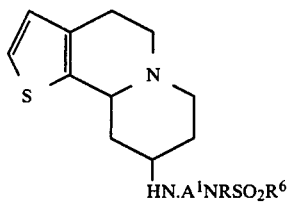

(XV)

(wherein $A^1$, R and $R^6$ have the meanings given above) may be reacted with a reactive derivative of the sulphonic acid of formula (III) above, in an analogous manner to that described above in connection with the reaction of the thienoquinolizine (XIII). The thienoquinolizine (XV) may be prepared by known methods. For example the thienoquinolizine of formula (XIII) may be selectively sulphonated with the reactive derivative of the sulphonic acid (III) using the requisite amount of reactive derivative for forming the monosulphonamide (XV) rather than the disulphonamide; it may be necessary to block one of the amine groups in the diamine (XIV) with a protecting group and remove the protecting group after the sulphonation. The thienoquinolizine (XV) alternatively may be prepared by reductive amination of the ketone (IV) with an amine $NH_2A^1NRSO_2R^6$ (where $A^1$, R and $R^6$ have the meanings given above) and a hydride transfer agent such as sodium borohydride.

Another method of preparing the compounds of the invention in which $R^1$ is $-A^1-NR^5SO_2R^6$ comprises reaction of a thienoquinolizine of general formula

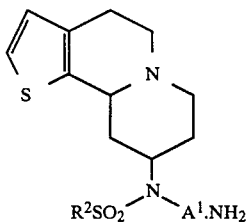

(XVI)

(where $A^1$ and $R^2$ are as defined above) with an appropriate reactive derivative of the sulphonic acid of formula (III) in an analogous manner to that described above in connection with the reaction of the thienoquinolizine (XIII). The thienoquinolizine starting material of formula (XVI) may be prepared by methods known per se. For example, a thienoquinolizine of general formula

(XVII)

(where $R^2$ has the meaning given above) may be reacted with a phthalimido protected haloamine of formula

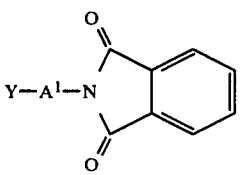

(XVIII)

(where $A^1$ has the meaning given above and Y is halogen, preferably bromine) in presence of a strong base such as sodium hydride or lithium diisopropylamide and the phthalimido protecting group removed.

Yet another method of preparing the compounds of the invention in which $R^1$ is $-A^1-NR^5SO_2R^6$ comprises reaction of a thienoquinolizine of formula (XVII) above with a compound of formula $$X-A^1-NRSO_2R^6 \quad (XIX)$$

(where X, $A^1$ and $R^6$ are as defined above) in presence of a strong base such as sodium hydride or lithium diisopropylamide.

If in the processes described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compound.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The compounds of the invention possess two asymmetric carbon atoms and hence can exist in various stereochemical forms. In addition they can exist as cis or trans isomers It will be realised that if the starting material (e.g. of formula II) is a mixture of isomers the product of formula (I) will also be a mixture of isomers unless the mixture is separated by standard procedures. The preferred compounds of the invention are the trans isomers in which the $-N(R^1).SO_2R^2$ group is the equatorial position, i.e. compounds of the general formula

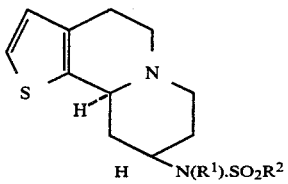
(XX)

and the pharmaceutically acceptable acid addition salts thereof. These compounds can be prepared by the methods described above from the corresponding trans isomer starting material. Resolution of a racemic final product or intermediate may be carried out by known procedures so as to give the product as an optically active enantiomorph.

The compounds of the present invention possess pharmacological activity. For example, the compounds, in general, possess $\alpha_2$-adrenoceptor antagonistic activity in warm blooded animals and hence are of value in conditions where antagonism of the $\alpha_2$-adrenoceptor is desirable, for example, as antidepressants, in treatment of diabetes and in inhibiting blood platelet aggregation.

The compounds of the invention are tested for $\alpha_2$-adrenoceptor antagonistic activity on the rat field stimulated vas deferens preparation using a modification of the method of Drew, Eur. J. Pharmac., 1977, 42, 123–130. The procedure is described below.

Desheathed vasa deferentia from sexually mature rats were suspended in a 6 ml organ bath in Krebs solution at 37° and bubbled with 5% $CO_2$ in oxygen. Platinum ring electrodes were positioned above and below the tissue for field stimulation, the stimulus parameters being 0.1 Hz 1 ms pulse width at supramaximal voltage. Twitch responses were recorded isotonically with a 0.5 g loading. Clonidine hydrochloride was used as the $\alpha$-adrenoceptor agonist and cumulative concentration-response curves were constructed for the inhibition of twitch obtained with clonidine in the range 0.125 to 4 ng $ml^{-1}$. After washing out clonidine, the twitch response quickly recovered and an antagonist was then introduced into the Krebs reservoir. Clonidine concentration-response curves were repeated 90 min after introduction of the antagonist. The concentration of clonidine producing 50% inhibition of twitch before and after introduction of antagonist were obtained and the dose-ratio for clonidine was calculated. Various concentrations of the antagonists were used.

These results were plotted in the manner described by Arunlakshana & Schild, Br.J.Pharmac. Chemother., 1959, 14, 48–58 and the values of $pA_2$ and slope were calculated. The compounds of the invention possess potent $\alpha_2$-adrenoceptor antagonistic activity. For example, N-(4,5,8,9,10,10a$\alpha$-hexahydro-7H-thieno[2,3-a]quinolizin-9$\beta$-yl)-N-methylpropanesulphonamide and N-(4,5,8,9$\alpha$,10,10a$\alpha$-hexahydro-7H-thieno[2,3-a]quinolizin-9-yl)-N-(2-ethanesulphonamidoethyl)-ethanesulphonamide, representative compounds of the invention, have been found to have a $pA_2$ for $\alpha_2$-adrenoceptor antagonistic activity of 7.5 and 7.31 respectively.

The compounds of the invention generally antagonise the $\alpha_2$-adrenoceptors to a much greater extent than the $\alpha_1$-adrenoceptors. The $\alpha_1$ antagonistic activity can be evaluated by a number of different methods. One method involves assessing the activity on the isolated anococcygeus muscle of the rat. The method is based on that of Gillespie, Br.J.Pharmac., 1972, 45, 404–416. In the procedure male rats (250–360g) are killed by a blow on the head and bled. The two anococcygeus muscles are removed from their position in the midline of the pelvic cavity, where they arise from the upper coccygeal vertebrae. The muscles are suspended in 5 ml organ baths in Krebs solution containing $10^{-4}$M ascorbic acid, to prevent drug oxidation. The tissues are gassed with a 95% oxygen, 5% $CO_2$ mixture and maintained at 37°. Longitudinal muscle contractions are recorded using isotonic transducers. Cumulative dose response curves are then obtained to phenylephrine or in some cases methoxamine, both agents being presynaptic alpha adrenoceptor agonists. The concentration range of phenylephrine or methoxamine used is 0.02 to 0.8 $\mu g.ml^{-1}$. The agonist is then washed from the bath and the test drug added to the bathing medium at a concentration of $10^{-6}$M. After 30 min equilibration with the test drug a further agonist dose response curve is obtained. The washing, equilibration and agonists dosing procedures are then repeated using $10^{-5}$M and $10^{-4}$M solutions of the test drug. Estimates of the $pA_2$ value for the test drug as an antagonist of phenylephrine or methoxamine were made from the agonist dose-ratios using the method of Arunlakshana & Schild, Br. J. Pharmac. Chemother., 1959, 14, 48–58.

The $pA_2$ values for $\alpha_1$ antagonistic activity for N-(4,5,8,9,10,10a$\alpha$-hexahydro-7H-thieno[2,3-a]quinolizin-9$\beta$-yl)-N-methylpropanesulphonamide and N-(4,5,8,9$\alpha$,10,10a$\alpha$-hexahydro-7H-thieno[2,3-a]quinolizin-9-yl)-N-(2-ethanesulphonamidoethyl)ethane sulphonamide have been found to be 5.9 and 5.18 respectively and the $\alpha_2/\alpha_1$ selectivity [i.e. antilog of ($\alpha_2 pA_2 - \alpha_1 pA_2$)] for these compounds are respectively 40 and 132. The compounds show selectivity towards the $\alpha_2$ receptors.

The invention further provides a compound of formula (I) or a pharmaceutically acceptable acid addition salt for use in antagonising $\alpha_2$-adrenoceptors in a mammal.

Compounds of the invention in which $R^1$ is hydrogen are useful as antihypertensive agents.

The invention also provides a pharmaceutical composition comprising a compound of general formula (II) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient. The invention also includes the compounds in the absence of the carrier where the compounds are in unit dosage form.

The following Examples illustrate the invention:

EXAMPLE 1

4,5,8,9,10,10a$\alpha$-Hexahydro-9$\beta$-methylamino-7H-thieno[2,3-a]quinolizine (a) A solution of thiophene-3-acetonitrile (25 g) in THF (150 mL) was treated with 1M BH$_3$.THF (340 mL) and stirred at room temperature under argon for 3 hours. The reaction was worked up by the addition of water followed by 6MHCl and stirred for ~$\frac{1}{2}$ hour. The THF was evaporated off, the residue basified and extracted into dichloromethane, dried (Na$_2$SO$_4$) and evaporated to an oil. The oil was subjected to acid-base extraction followed by azeotroping with toluene. Yield 10 g.

(b) The amine from step (a) (10 g) was heated under reflux in ethyl formate for 4 hours. The reaction mixture was evaporated to an oil and distilled b.p. 200°–205° at 3 mbar. Yield 9.5 g.

(c) The formamide from step (b) (9 g) in dry, ethanol free chloroform (100 mL) was added dropwise over a period of 90 mins to a solution of phosphorus pentachloride (12.1 g) in dry chloroform (120 mL) at room temperature under argon. After 3 hours the reaction was poured on to 2M sodium hydroxide, extracted into dichloromethane, dried (Na$_2$SO$_4$) and evaporated to an oil. Yield 4 g.

(d) The dihydrothienopyridine from step (c) (4 g) in dichloroethane (50 mL) was treated with gaseous HCl for 30 mins. Methyl vinyl ketone (2.6 mL) was added slowly to a stirred reaction mixture at reflux under argon. After 1 hour the addition was completed, the reaction mixture allowed to cool to room temperature, filtered, washed with acetone and dried. Yield 4.8 g.

(e) A fine suspension of the ketone from step (d) (4.7 g) in 2-propanol (50 mL) under argon was treated with 33% solution of methylamine in ethanol (6.9 mL) over 15 min. with ice-water cooling (temp 10°–15° C.). After stirring for a further 2 hours, sodium hydroxide (1.55 g) was added, followed by sodium borohydride (1.2 g) portionwise over 1 hour. The reaction was stirred for 1 hour at about 10° C. then worked up by removal of half the isopropanol at reduced pressure, dilution with water (50 mL) followed by extraction into dichloromethane. The extract was washed with water, dried (Na$_2$SO$_4$) and evaporated to an oil (4.2 g). The oil was dissolved in Et$_2$O/IPA and treated with ethereal HCl. The resulting oil was stirred until crystalline, filtered, recrystallised from IPA then triturated with CH$_3$CN yielding 2 g of the title compound as the dihydrochloride, m.p. 240°–2° C. The residues were chromatographed on SiO$_2$ (10% MeOH, 1% NH$_3$ 89% CHCl$_3$) yielding further 1 g of title base.

Analysis: Found: C, 47.2; H, 7.1; N, 9.0%. C$_{12}$H$_{18}$N$_2$S$\frac{1}{2}$H$_2$O requires: C, 47.4; H, 7.0; N, 9.2%.

EXAMPLE 2

N-(4,5,8,9,10,10a$\alpha$-hexahydro-7H-thieno[2,3-a]quinolizin-9$\beta$-yl)-N-methylpropanesulphonamide n-Propane sulphonylchloride (0.76 g) in dichloromethane (8 mL) was added dropwise to a stirred solution of 4,5,8,9,10,10a$\alpha$-hexahydro-9$\beta$-methylamino-7H-thieno[2,3-a]quinolizine (1.18 g) in dichloromethane (5 mL). After 3 hours at room temperature the reaction mixture was washed with 2M sodium hydroxide (2×5 mL) dried (Na$_2$SO$_4$) and evaporated to an oil which crystallised after chromatography on basic alumina/diethyl ether. The product was converted to the crystalline tosylate salt, 1.4 g, m.p. 176°–177° C.

Analysis: Found: C, 52.0; H, 6.1; N, 5.4%. C$_{15}$H$_{24}$N$_2$O$_2$S$_2$.C$_7$H$_7$SO$_3$H$\frac{1}{2}$H$_2$O requires: C, 51.9; H, 6.3; N, 5.4%.

EXAMPLE 3

N-(4,5,8,9,10,10a$\alpha$-hexahydro-7H-thieno[2,3-a]quinolizine-9$\beta$-yl)-N,2-dimethylpropanesulphonamide 2-Methyl propane sulphonyl chloride (0.21 g) in dichloromethane (1 mL) was added dropwise to a stirred solution of 4,5,8,9.10,10a$\alpha$-hexahydro-9$\beta$-methylamino-7H-thieno[2,3-a]quinolizine (400 mg) in dichloromethane (5 mL). After 2 hours at room temperature the reaction mixture was washed with 2M sodium hydroxide solution, dried (Na$_2$SO$_4$), evaporated to an oil and purified by chromatography on silica/Et$_2$O. The product was converted to a tosylate salt yield 230 mg, m.p. 212°–213° C.

Analysis: Found: C, 53.6; H, 6.6; N, 5.3%. C$_{16}$H$_{26}$N$_2$S$_2$O$_2$ C$_7$H$_7$SO$_3$H requires: C, 63.7; H, 6.6; N, 5.4%.

EXAMPLE 4

N-(4,5,8,9,10,10aα-hexahydro-7H-thienyl[2,3-a]quinolizin-9β-yl)-N-methyl sulphamide 4,5,8,9,10,10aα-Hexahydro-9β-methylamino-7H-thieno[2,3-a]quinolizine (530 mg) and sulphamide (600 mg) were heated under reflux for 24 hours. The solvent was removed under reduced pressure leaving a crystalline solid which was washed with water, and converted to the hydrochloride and recrystallised from 2-propanol affording 810 mg, m.p. 208°–209° C.

Analysis: Found: C, 42.2; H, 6.0; N, 12.0%. C$_{12}$H$_{18}$N$_3$O$_2$S$_2$ requires: C, 42.2; H, 5.8; N, 12.3%.

EXAMPLE 5

N-(4,5,8,9α,10,10aα-Hexahydro-7H-thieno[2,3-a]quinolizin-9-yl)-N-(2-ethanesulphonamidoethyl)ethane sulphonamide (a) The ketone from Example 1d, (0.87 g) in isopropanol (10 mL) was treated with ethylenediamine (1.4 mL) in ethanol (2 mL) at 0° C. Sufficient ethereal HCl was added to bring the pH to 8. After 24 hours tlc (EtOAc/SiO$_2$) shows no starting material remains. Solid NaOH (0.25 g) was added followed by NaBH$_4$ (0.35 g) portionwise over ~1 hour. After 3 hours the solvent was removed and the product partitioned between dichloromethane and water. The organic phase was separated, dried (Na$_2$SO$_4$) and evaporated to an oil. Yield 0.5 g.

(b) The diamine from Example 5a, in CH$_3$CN (3.5 mL) containing triethylamine (0.55 mL) was treated very slowly over 20 hours with ethanesulphonylchloride (0.51 g) in acetonitrile (10 mL). One hour after the addition was complete the solvent was evaporated off and the residue partitioned between dichloromethane and water. The organic phase was separated, dried (Na$_2$SO$_4$) and evaporated to an oil (0.7 g). The obtained monosulphonamide was used crude in the next stage.

(c) The crude product from Example 5(b) (0.7 g) in acetonitrile (10 mL) containing triethylamine (0.28 mL), was treated with ethanesulphonylchloride (0.25 g) in acetonitrile (4 mL) over 5–10 mins. After standing for 10 mins at room temperature absolute ethanol (91 mg) was added and the reaction allowed to stir for 5 mins. The solvent was evaporated off, the residue dissolved in chloroform and washed with a saturated sodium bicarbonate solution. The organic phase was dried (NaSO$_4$), evaporated down and dissolved in ethyl acetate and filtered through neutral Al$_2$O$_3$. The eluent was stirred with charcoal, filtered and evaporated to give the title compound as an oil which was converted to the acid maleate salt in ethylacetate, yielding 0.17 g, m.p. 145°–7° C.

Analysis: Found, C, 45.7; H, 6.4; N, 7.8%. C$_{17}$H$_{29}$N$_3$O$_4$S$_3$·C$_4$H$_4$O$_4$ requires C, 45.7; H, 6.0; N, 7.6%.

We claim:

1. A compound selected from the group consisting of a thienoquinolizine of the formula

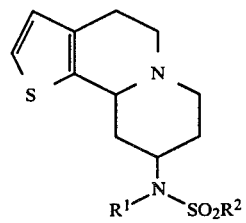

(I)

and a pharmaceutically acceptable acid addition salt thereof, where R$^1$ is —A$^1$NR$^5$.SO$_2$R$^6$ (where A$^1$ is a lower alkylene group having 1 to 3 carbon atoms in the chain between the two N atoms, R$^5$ is hydrogen or lower alkyl and R$^6$ is lower alkyl, halo(lower)alkyl, phenyl or phenyl substituted by one or more substituents selected from the group consisting of halogen, lower alkoxy, lower alkyl, loweralkylenedioxy, nitro, amino, loweralkylcarbonylamino, lower alkylamino, diloweralkylamino or trifluoromethyl) and R$^2$ is lower alkyl, halo(lower)alkyl, phenyl or phenyl substituted by one or more substituents selected from the group consisting of halogen, lower alkoxy, lower alkyl, lower alkylenedioxy, nitro, amino, loweralkylcarbonylamino, lower alkylamino, diloweralkylamino or trifluoromethyl.

2. A compound according to claim 1 wherein R$^2$ is lower alkyl.

3. A compound according to claim 1 which is N-(4,5,8,9a,10,10aα-hexahydro-7H-thieno[2,3-a]quinolizin-9-yl)-N-(2-ethanesulphonamidoethyl)ethane sulphonamide or a pharmaceutically acceptacle acid addition salt thereof.

4. A composition having α$_2$-adrenoceptor antagonistic activity comprising an amount sufficient to antagonise α$_2$ adrenoceptors of a compound selected from the group consisting of a thienoquinolizine of the formula

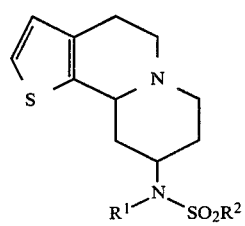

(I)

and a pharmaceutically acceptable acid addition salt thereof, where R$^1$ is —A$^1$NR$^5$.SO$_2$R$^6$ (where A$^1$ is a lower alkylene group having 1 to 3 carbon atoms in the chain between the two N atoms, R$^5$ is hydrogen or lower alkyl and R$^6$ is lower alkyl, halo(lower)alkyl, phenyl or phenyl substituted by one or more substituents selected from the group consisting of halogen, lower alkoxy, lower alkyl, loweralkylenedioxy, nitro, amino, loweralkylcarbonylamino, lower alkylamino, diloweralkylamino or trifluoromethyl) and R$^2$ is lower alkyl, halo(lower)alkyl, phenyl or phenyl substituted by one or more substituents selected from the group consisting of halogen, lower alkoxy, lower alkyl, loweralkylenedioxy, nitro, amino, loweralkylcarbonylamino, lower alkylamino, diloweralkylamino or trifluoromethyl in association with a pharmaceutically acceptable carrier.

5. A method of antagonising $\alpha_2$ adrenoceptors in warm blooded animals which comprises administering to the animal an amount sufficient to antagonise $\alpha_2$ adrenoceptors of a compound selected from the group consisting of a thienoquinolizine of the formula

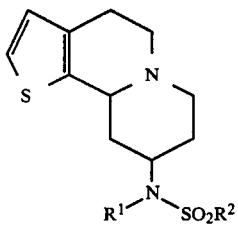

and a pharmaceutically acceptable acid addition salt thereof, where $R^1$ is $—A^1NR^5.SO_2R^6$ (wherein $A^1$ is a lower alkylene group having 1 to 3 carbon atoms in the chain between the two N atoms, $R^5$ is hydrogen or lower alkyl and $R^6$ is lower alkyl, halo(lower)alkyl, phenyl or phenyl substituted by one or more substituents selected from the group consisting of halogen, lower alkoxy, lower alkyl, loweralkylenedioxy, nitro, amino, loweralkylcarbonylamino, lower alkylamino, diloweralkylamino or trifluoromethyl) and $R^2$ is lower alkyl, halo(lower)alkyl, phenyl or phenyl suhstituted by one or more substituents selected from the group consisting of halogen, lower alkoxy, lower alkyl, loweralkylenedioxy, nitro, amino, loweralkylcarbonylamino, lower alkylamino, diloweralkylamino or trifluoromethyl.

* * * * *